United States Patent
Fujita et al.

(10) Patent No.: US 7,375,329 B2
(45) Date of Patent: May 20, 2008

(54) SCANNING ELECTRON MICROSCOPE

(75) Inventors: Masashi Fujita, Hitachinaka (JP); Hiroki Kawada, Tsuchiura (JP); Satoru Iwama, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1 day.

(21) Appl. No.: 11/324,311

(22) Filed: Jan. 4, 2006

(65) Prior Publication Data
US 2006/0108527 A1 May 25, 2006

Related U.S. Application Data

(63) Continuation of application No. 11/000,522, filed on Dec. 1, 2004, now Pat. No. 6,995,370.

(30) Foreign Application Priority Data

Dec. 5, 2003 (JP) ............................. 2003-407984

(51) Int. Cl.
- H01J 37/26 (2006.01)
- G01B 11/00 (2006.01)
- G06K 9/00 (2006.01)

(52) U.S. Cl. .................. 250/310; 250/311; 250/396 R; 250/397; 250/399; 250/306; 250/307

(58) Field of Classification Search ................. 250/310; 382/145
See application file for complete search history.

(56) References Cited

U.S. PATENT DOCUMENTS

| | | | |
|---|---|---|---|
| 4,851,768 A * | 7/1989 | Yoshizawa et al. | 324/751 |
| 5,046,012 A * | 9/1991 | Morishita et al. | 700/121 |
| 5,134,289 A * | 7/1992 | Murakoshi et al. | 250/311 |
| 5,436,448 A | 7/1995 | Hosaka et al. | |
| 5,533,139 A * | 7/1996 | Parker et al. | 382/108 |

(Continued)

FOREIGN PATENT DOCUMENTS

JP 04-209457 7/1992

(Continued)

OTHER PUBLICATIONS

Japanese Office Action, issued in corresponding Japanese Patent Application No. 2003-407984, drafted on Sep. 13, 2007.

*Primary Examiner*—David Vanore
*Assistant Examiner*—Bernard Souw
(74) *Attorney, Agent, or Firm*—McDermott Will & Emery LLP

(57) ABSTRACT

In a scanning electron microscope, slimming is reduced by reducing a frame count. As the frame count is reduced, the amount of detected secondary electrons decreases, so that a probe current amount is increased to emit an increased amount of detected secondary electrons. A primary electron beam is scanned on a sample, a histogram is created, and the histogram is second-order differentiated to calculate a level of halftone at which a sample image changes in contrast, and to calculate the probe current amount. By adjusting the frame count suitable for the calculated probe current amount, and the contrast suitable for the sample image, the slimming of the sample is limited, and a highly visible sample image is generated for length measurement.

10 Claims, 7 Drawing Sheets

U.S. PATENT DOCUMENTS

| | | | |
|---|---|---|---|
| 5,600,734 A | | 2/1997 | Okubo et al. |
| 5,825,912 A | | 10/1998 | Okubo et al. |
| 5,872,862 A | | 2/1999 | Okubo et al. |
| 6,166,380 A | * | 12/2000 | Kitagawa et al. ............. 250/307 |
| 6,476,388 B1 | | 11/2002 | Nakagaki et al. |
| 6,515,296 B1 | * | 2/2003 | Komatsu et al. ....... 250/559.44 |
| 6,538,249 B1 | * | 3/2003 | Takane et al. ............... 250/310 |
| 6,653,633 B2 | * | 11/2003 | Takane et al. ............... 250/310 |
| 6,738,527 B2 | | 5/2004 | Kuwata et al. |
| 6,822,245 B2 | * | 11/2004 | Muto et al. ............ 250/492.21 |
| 6,825,480 B1 | * | 11/2004 | Watanabe et al. ........ 250/491.1 |
| 6,936,818 B2 | * | 8/2005 | Takane et al. ............... 250/310 |
| 6,995,370 B2 | * | 2/2006 | Fujita et al. ................. 250/310 |
| 7,109,485 B2 | * | 9/2006 | Takane et al. ............... 250/310 |
| 2002/0171852 A1 | | 11/2002 | Zhang et al. |
| 2003/0012437 A1 | | 1/2003 | Zaklika et al. |
| 2003/0118233 A1 | * | 6/2003 | Olsson ....................... 382/173 |
| 2004/0086168 A1 | | 5/2004 | Kuwabara |
| 2004/0091169 A1 | | 5/2004 | Park et al. |
| 2004/0096121 A1 | | 5/2004 | Kanatsu et al. |
| 2004/0189818 A1 | | 9/2004 | Tsuruoka et al. |
| 2005/0123195 A1 | * | 6/2005 | Takarada ..................... 382/172 |
| 2005/0139772 A1 | * | 6/2005 | Hasegawa et al. ........... 250/311 |
| 2005/0145791 A1 | * | 7/2005 | Fujita et al. ................. 250/311 |
| 2006/0108527 A1 | * | 5/2006 | Fujita et al. ................. 250/310 |
| 2006/0269129 A1 | * | 11/2006 | Tanigawa ................... 382/169 |
| 2007/0023657 A1 | * | 2/2007 | Takane et al. ............... 250/310 |
| 2007/0147676 A1 | * | 6/2007 | Sasai ......................... 382/149 |

FOREIGN PATENT DOCUMENTS

| | | |
|---|---|---|
| JP | 7-240166 A | 9/1995 |
| JP | 11-176367 | 7/1999 |
| JP | 2001-243907 | 9/2001 |

* cited by examiner

SCANNING ELECTRON MICROSCOPE

RELATED APPLICATIONS

This application is a continuation of application Ser. No. 11/000,522, filed on Dec. 1, 2004, now U.S. Pat. No. 6,995,370 which in turn claims the benefit of Japanese Application No. 2003-407984, filed on Dec. 5, 2003, the disclosures of which Applications are incorporated by reference herein.

BACKGROUND OF THE INVENTION

The present invention relates to a scanning electron microscope for observing a miniature pattern to measure dimensions thereof, and more particularly, to a scanning electron microscope for observing and measuring a sample, the shape of which can be deformed by an electron beam irradiated thereto.

Scanning electron microscopes (SEM) are widely used in manufacturing and testing steps of a functional product such as a semiconductor device, a thin film magnetic head, and the like, which are fabricated by micro-machining the surface thereof, for measuring widths of processed patterns and inspecting the appearance of resulting products. The scanning electron microscope is an apparatus for forming the image of a sample by narrowing down an electron beam emitted from an electron source with a converging lens or an objective lens which makes use of an interaction of a magnetic field or an electric field with the electron beam, one-dimensionally or two-dimensionally scanning the electron beam on the sample using a deflector, detecting a secondary signal (secondary electrons, reflected electrons, or electromagnetic waves) with a detector which makes use of an opto-electric effect or the like, and converting the detected signal into a viewable signal such as a luminance signal synchronized to the scanning of the electron beam. Considerable efforts have been put into the scanning electron microscope to provide a sample image which accurately corresponds to the shape of the surface of the sample under observation and length measurement, and the distance between arbitrary two points is calculated on the surface of the sample from the sample image thus generated. This calculation is commonly called "length measurement," and a scanning electron microscope having such a calculation function is called a "length measuring SEM." Such a scanning electron microscope irradiates the surface of a sample under observation with an electron beam having accessible energy of several hundreds of electronvolts, as a matter of course.

On the other hand, further miniaturization has been advanced in recent years in the micro-machining on the surface of semiconductor, and a photoresist which reacts to argon fluoride (ArF) excimer laser light (hereinafter called the "ArF resist") has been used for a photosensitive material of photolithography. Because of its wavelength as short as 193 nm, the ArF laser light is regarded as suitable for exposure to more miniature circuit patterns. However, the results of recent investigations have revealed that the ArF resist is highly vulnerable to electron beam irradiation, and when a formed pattern is observed or measured with a scanning electron microscope, the scanning of a converged electron beam causes a condensation reaction in a base acrylic resin or the like, resulting in a reduction in volume (hereinafter called "slimming") and an eventual change in the shape of a circuit pattern.

It is said that for reducing the slimming of the ArF resist, it is effective to reduce an irradiation density of an electron beam to a sample. However, a reduction in the irradiation density of an electron beam causes a reduction in the amount of secondary electrons generated from the sample, resulting in a dark image. Therefore, there is a need for a method of limiting the slimming and generating a highly visible image.

For generating a highly visible image, an optimal brightness and contrast must be defined for a sample image. In the prior art, the brightness and contrast of a sample image are adjusted by changing condition settings for a detector and an amplifier. JP-A-7-240166 describes a contrast adjusting method using a contrast level conversion function.

In the prior art method mentioned above, when a micro-machined ArF resist pattern is measured twice under the conditions of a frame count equal to 16, and a probe current amount equal to 24 pA, a slimming amount of 1.3 nm occurs between the first and second length measurements, demonstrating a failure in sufficiently reducing the slimming in the length measurement of the micro-machined ArF resist pattern. Disadvantageously, the prior art method of reducing the slimming does not take into consideration an image control technique which relies on the relationship between the number of times of electron beam scanning required for creating a sample image (hereinafter called the "frame count") and the probe current amount, and fails to sufficiently reduce the slimming and generate a highly visible sample image.

SUMMARY OF THE INVENTION

It is an object of the present invention to provide a scanning electron microscope which is capable of reducing the influence of slimming to produce a highly visible sample image when it is used to observe or measure a sample, such as an ArF resist, which is vulnerable to electron beam irradiation and can suffer from slimming.

An experiment made by the inventors found that the slimming of the ArF resist is deeply related to a frame count, and that the probe current amount and an accelerating voltage do not significantly affect the slimming. While it has been conventionally believed that the slimming is affected by the electron beam irradiation density, the result of the experiment convinces that the ArF resist has different properties from other resists.

FIGS. 2A-2C show the relationship between the number of times of length measurements and slimming when an ArF resist having a consistent pattern was measured while a frame count, the probe current amount, and an accelerating voltage were varied. FIG. 2A shows the relationship between the slimming and the number of times of length measurements when the frame count was varied under the conditions of the accelerating voltage equal to 500 V and the probe current amount (current amount of primary electron beam) equal to 24 pA. It can be seen in FIG. 2A that the slimming is reduced as the frame count is smaller. It is understood that as the frame count is reduced to one half, the slimming can be reduced by 2-2.3 nm each time the frame count is incremented by one. FIG. 2B shows the relationship between the slimming and the number of times of length measurements when the probe current amount is varied under the condition of the frame count equal to eight, and the accelerating voltage equal to 500 V. It can be said that even though the probe current amount is varied, the slimming is not significantly affected by the variations in the probe current amount, taking into account the length measurement repeatability (3σ). FIG. 2C shows the relationship between the slimming and the number of times of length measurements when the accelerating voltage was varied under the conditions of the frame count equal to eight, and the probe current amount equal to 24 pA. As is the case with the probe current amount, it can be said that variations in the accelerating voltage does not either significantly affect the slimming, taking into account the length measurement repeatability.

From the foregoing results, it is understood that a reduction in the frame count is most effective for reducing the slimming. As mentioned above, it has been conventionally said that the slimming is effectively reduced by reducing the electron beam irradiation density, i.e., reducing the frame count in this case, and by reducing the probe current amount. However, with the ArF resist, it is concluded that while the frame count does affect the slimming, the probe current amount does not affect the slimming. This result is different from the conventional common sense.

However, when the frame count is reduced for reducing the slimming, an insufficient number of times of scanning for creating a sample image causes a smaller amount of detected secondary electrons, which would give rise to such problems as lower contrast and the generation of noise due to a lower S/N ratio. To avoid these problems, the present invention increases the probe current amount, which does not significantly affect the slimming, to detect an increased amount of secondary electrons emitted from a sample, thereby ensuring an image quality equivalent to a sample image generated by the conventional method, even though the frame count is reduced (hereinafter called the "low frame scanning scheme").

In the prior art, a histogram is created for a generated sample image, the average of the histogram is defined as the brightness of the sample image, and the brightness is controlled by increasing the dynamic range of an amplifier. Then, the standard deviation of the histogram is defined as the contrast of the sample image, and the contrast is controlled by a detecting condition of a detector. With this conventional control method, when the low frame scanning scheme is performed, the histogram largely shifts due to large variations in the probe current amount, so that the sample image must be scanned repeatedly to control the histogram, and the histogram must be created again. Even if the slimming is reduced by reducing the frame count, the repeated scanning of the electron beam, for creating the histogram, results in an increased amount of slimming. A need therefore exists for a method of reducing surplus electron beam scanning by minimizing the number of times the histogram is created and calculating a brightness and contrast optimal for a sample image.

In the present invention, therefore, the luminance of each pixel in a sample image generated by electron beam scanning is divided, for example, into 256 levels of halftone to create a luminance histogram which indicates the number of pixels at each level of halftone. Then, the luminance histogram is relied on to calculate the probe current amount and the frame count which provide appropriate contrast and brightness of the image. The calculated probe current amount and frame count are set in the apparatus to form a sample image for measurement.

Specifically, a scanning electron microscope of the present invention includes an electron beam source, a lens system for converging a primary electron beam emitted from the electron beam source onto the surface of a sample, a scanning unit for tow-dimensionally scanning the converged primary electron beam on the surface of the sample, a detector for detecting a secondary signal generated from the sample irradiated with the primary electron beam, an amplifier for amplifying a signal detected by the detector, a drawing unit for forming a sample image based on the signal amplified by the amplifier, and a control processing unit. The control processing unit creates a luminance histogram of a sample image, controls a current value of the primary electron beam such that the brightness of the image calculated from the luminance histogram is located substantially at the center of an overall halftone width, and controls an amplifying condition for the amplifier to provide a contrast corresponding to the brightness of the image.

The control processing unit typically derives a function from the luminance histogram, draws a curve representative of the function, calculates two halftone levels at which a second-order differential of the function takes maxima in a lower halftone region and a higher halftone region of the curve, and controls the amplifying condition for the amplifier such that the two halftone levels are included in a predetermined halftone range.

When the curve representative of the function derived from the histogram has a peak in a lower halftone end region, the control processing unit creates a virtual histogram by replacing the peak region of the histogram with a tangential line which is tangential to a lower halftone region of the curve and intersects with a halftone level axis, and controls the current value of the primary electron beam such that the brightness of the image calculated from the virtual histogram is located substantially at the center of the overall halftone width. In this event, the control processing unit controls the amplifying condition for the amplifier such that a halftone level at which the tangential line intersects with the halftone level axis, and a halftone level at which the second-order differential takes a maximum in a higher halftone region of the curve are included in the predetermined halftone range.

When the curve representative of the function derived from the histogram has a peak in a higher halftone end region, the control processing unit creates a virtual histogram by replacing the peak region of the histogram with a tangential line which is tangential to a higher halftone region of the curve and intersects with the halftone level axis, and controls the current value of the primary electron beam such that the brightness of the image calculated from the virtual histogram is located substantially at the center of the overall halftone width. In this event, the control processing unit controls the amplifying condition for the amplifier such that a halftone level at which the tangential line intersects with the halftone level axis, and a halftone level at which the second-order differential takes a maximum in a lower halftone region of the curve are included in the predetermined halftone range.

The electron beam microscope of the present invention creates a histogram of a sample image, and can find a minimum frame count from a calculated probe current amount based on halftone levels near the border of a sample and a background. By observing the sample under the conditions of the calculated probe current amount and the minimum frame count, a highly visible image can be displayed while limiting the slimming of the sample. In addition, the throughput can be improved by the low frame scanning scheme with the minimum frame count and the histogram control method of the present invention.

Other objects, features and advantages of the invention will become apparent from the following description of the embodiments of the invention taken in conjunction with the accompanying drawings.

DETAILED DESCRIPTION OF THE EMBODIMENTS

In the following, embodiments of the present invention will be described with reference to the accompanying drawings.

Figure 1:
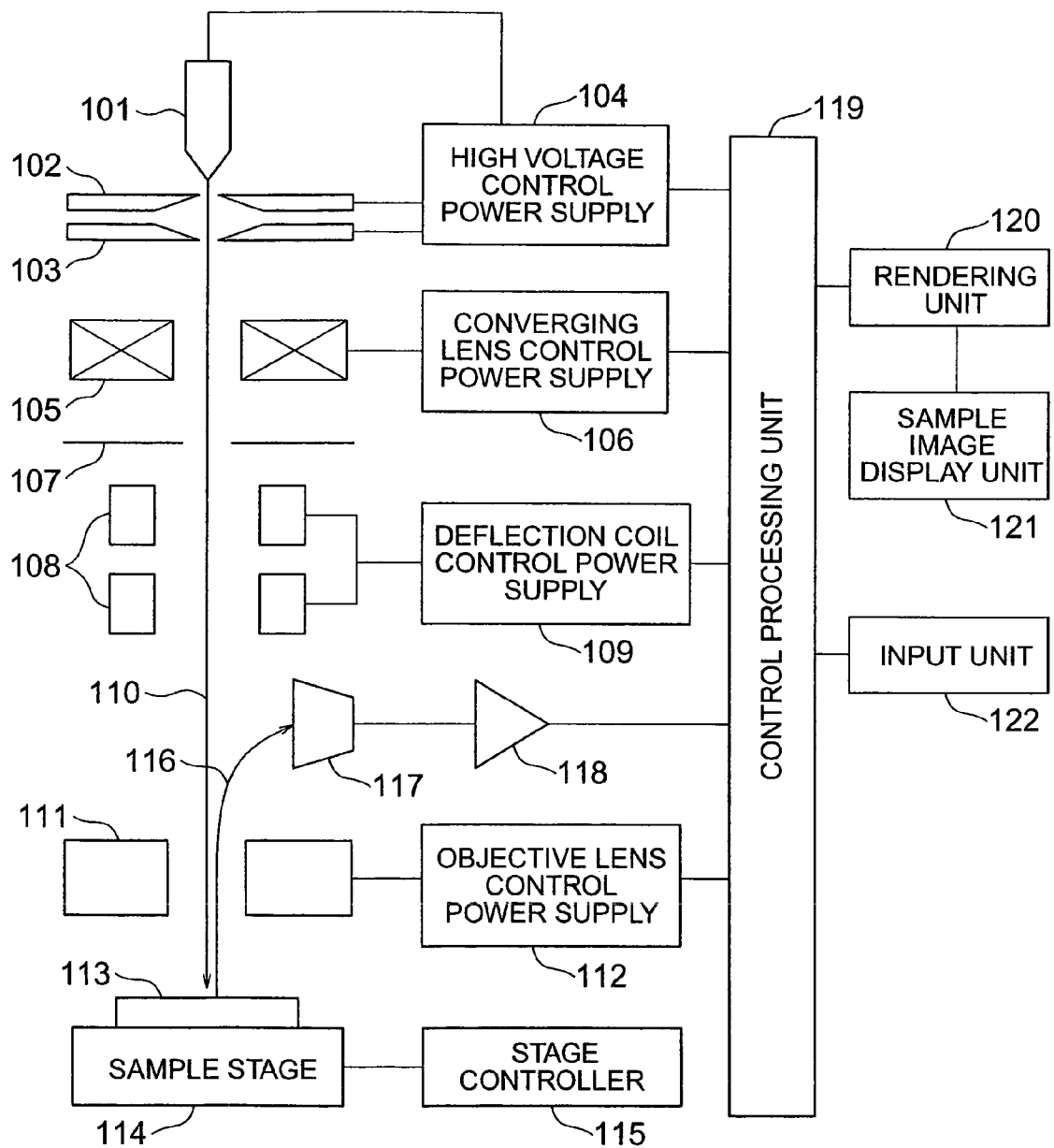
FIG. 1 is a block diagram generally illustrating an electron microscope which has a low frame length measurement function according to the present invention.
Figure 2A:
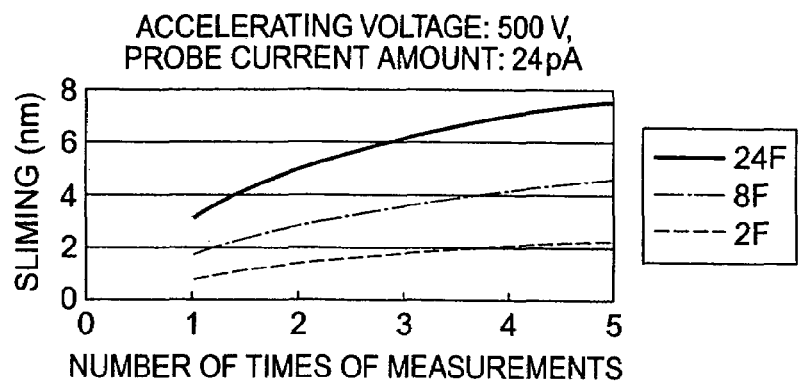
FIG. 2A is a graph showing the relationship between the number of times of length measurements and the slimming when a frame count is varied.
Figure 2B:
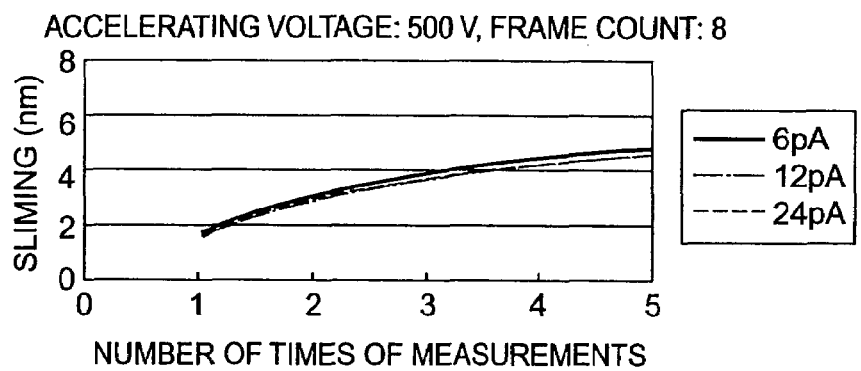
FIG. 2B is a graph showing the number of times of length measurements and the slimming when the probe current amount is varied.
Figure 2C:
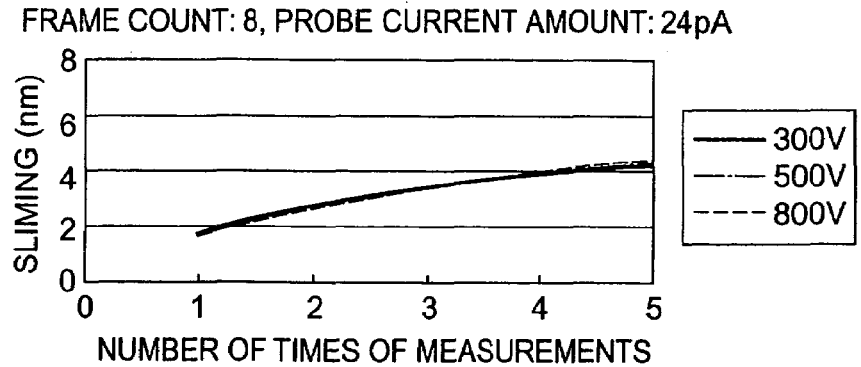
FIG. 2C is a graph showing the relationship between the number of times of length measurements and the slimming when an accelerating voltage is varied.

FIG. 1 is a block diagram generally illustrating a scanning electron microscope according to the present invention. A voltage is applied between a cathode 101 and a first anode 102 by a high voltage control power supply 104 which is controlled by a control processing unit 119 to draw a predetermined emission current from the cathode 101. Since an accelerating voltage is applied between the cathode 101 and a second anode 103 by the high voltage control power supply 104 controlled by the control processing unit 119, a primary electron beam 110 emitted from the cathode 101 is accelerated to travel to a subsequent lens system. The primary electron beam 110 is converged by a convergence lens 105 controlled by a convergence lens control power supply 106, and an unnecessary region of the primary electron beam 110 is removed by an aperture plate 107. Then, the primary electron beam 110 is converged by an objective lens 111 controlled by an objective lens control power supply 112 into a miniature spot which is two-dimensionally scanned on a sample 113 by a deflection coil 108. A scanning signal of the deflection coil 108 is controlled by a deflection coil control power supply 109 in accordance with an observation scaling factor. The sample 113 is fixed on a sample stage 114 in such a manner that it is two-dimensionally movable. The sample stage 114 is moved by a stage controller 115. Secondary electrons 116 emitted from the sample 114 irradiated with the primary electron beam 110 are detected by a secondary electron detector 117, and amplified by an amplifier 118. A rendering unit 120 converts the detected secondary electron signal to a visible signal which is appropriately arranged on a different plane, thereby displaying an image adapted to the surface shape of the sample 113 on a sample display unit 121. An input unit 122 interfaces the operator with the control processing unit 119, such that the operator gives instructions through the input unit 122 to control the aforementioned units, specify a measuring point, and measure dimensions at the specified point.

Figure 3:
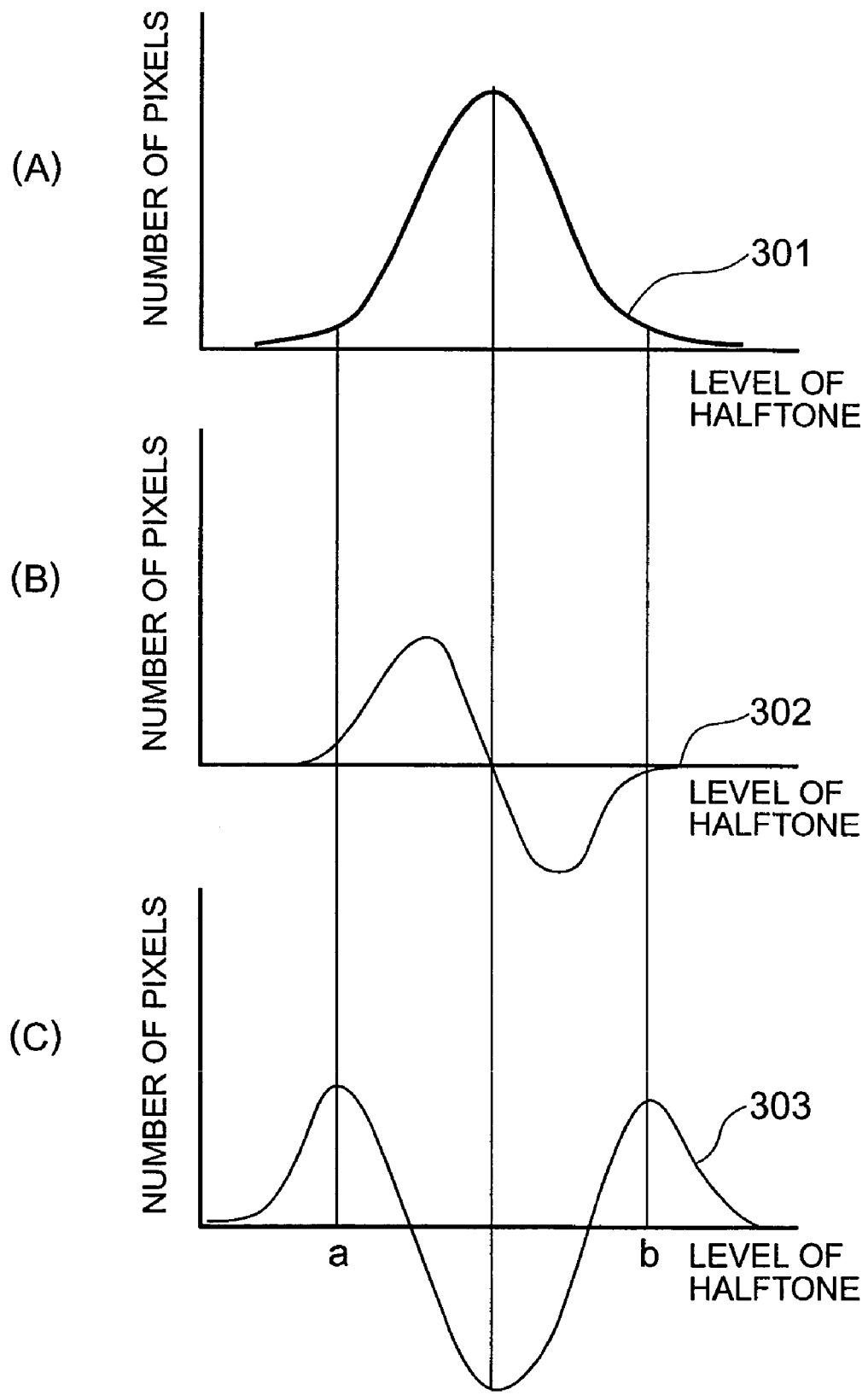
FIG. 3 shows an example of a luminance histogram of a sample image, and a first-order differential graph and a second-order differential graph of the histogram.

Next, description will be made on a method of controlling the electron microscope based on a luminance histogram for a sample image. FIG. 3(A) is a diagram showing an example of a luminance histogram for a sample image, where the horizontal axis represents the level of halftone, and the vertical axis represents the number of pixels. The luminance histogram is differentiated once to create a first-order differential graph 302 shown in FIG. 3(B), and twice to create a second-order differential graph 303 shown in FIG. 3(C). Halftone levels a, b, at which the second-order differential graph 303 takes maxima, are thought to represent the neighborhood of a border between the sample image and background in the histogram 301 (hereinafter called the "border point"). In this embodiment, since the there are 256 levels of halftone ranging from 0 to 255, the histogram control is required to limit the border points at both ends within the 255 levels of halftone.

Figure 4A:
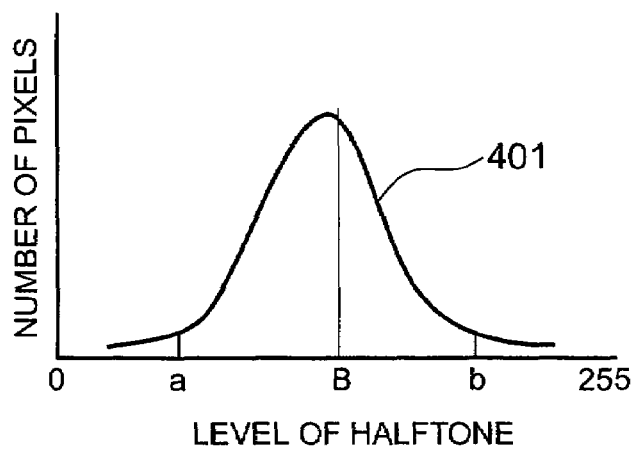
FIGS. 4A-4C are graphs generally showing an exemplary histogram control method.
Figure 4B:
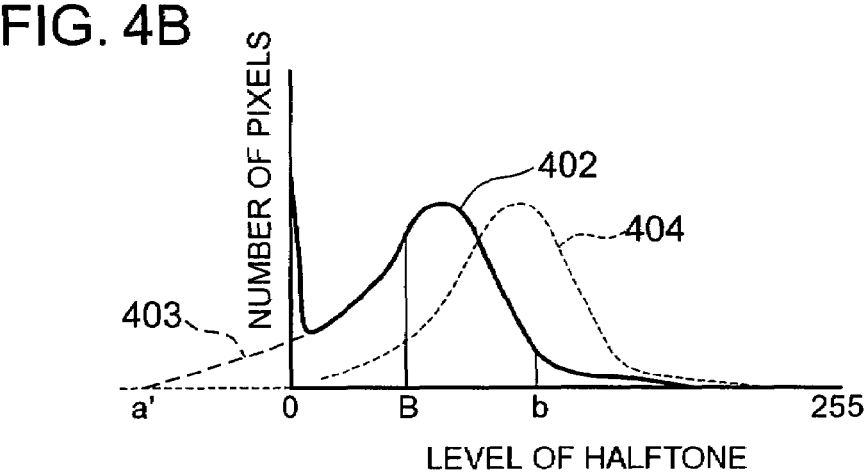
Figure 4C:
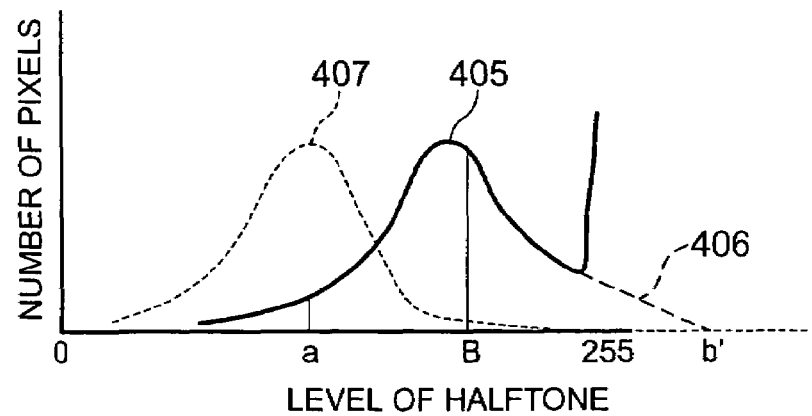

FIGS. 4A-4C are diagrams showing an exemplary luminance histogram of a sample image created by the sample display unit. As shown in FIG. 4A, the two border points a, b exist on curved sections at both ends of the luminance histogram. The border point a represents a border between the darkest region of the background and the sample image, while the border point b represents a border between the brightest region of the background and the sample image (edges of the sample). The border points a, b shown in FIG. 4A are the same as the halftone points a, b at which the second-order differential graph 303 of the luminance histogram, described in connection with FIG. 3, reaches the maxima.

Since the histogram control is only required to consider the existence of the border points a, b at both ends, the histogram 401 is second-order differentiated in both end regions to find the border points a, b. The image is regarded as highly visible if the two border points exist on the histogram, and the width of the histogram falls within the 256 levels of halftone. Therefore, the brightness of the sample image is adjusted by the average value of the histogram, and the contrast is mainly adjusted by the dynamic range of the amplifier 118 in the secondary electron detector 117 such that the two border points existing at both extreme ends fall under the 256 levels of halftone.

When the border points exist at both ends of the histogram as in FIG. 4A, the brightness B of the image is calculated by:

$$B = S/N \quad (1)$$

where S is an area when the histogram is integrated, and N is the total number of pixels.

The probe current amount is controlled such that the brightness B is shifted to the position of a halftone level X substantially at the center, for example, a halftone level 130. Since the brightness is generally proportional to the probe current, the following Equation (2) is established, and the probe current amount $I_P$ is found by Equation (3):

$$S/N : I_O = X : I_P \quad (2)$$

$$I_P = X \cdot I_O \cdot N/S \quad (3)$$

where $I_O$ is the probe current before the control is conducted, and $I_P$ is the probe current at which the brightness B reaches a halftone level X.

Next, a minimum frame count, by which the scanning can be made, is calculated based on the calculated probe current amount. Since there is a relationship between the probe current $I_P$ and the required frame count F, represented by $I_P \times F = A$ (constant), the frame count is calculated in accordance with this equation. The constant A differs from one sample to another. The contrast control is conducted by adjusting the dynamic range of the amplifier 118 such that the halftone width (b-a) between the halftone levels a, b at the border points, found by the second-order differential, falls within the 256 levels of halftone.

When the sample image is too dark, the resulting histogram shifts to the left (toward the lower level of halftone) as shown in FIG. 4B, where the number of pixels is increased in a lower halftone end region including the level 0 of halftone, and a peak appears at the lower end of halftone. Conversely, when the sample image is too bright, the histogram shifts to the right (toward the higher level of halftone) as shown in FIG. 4C, where the number of pixels is increased in a higher halftone end region including the level 255 of halftone, and a peak appears at the higher end of halftone. In FIG. 4B, the border point a on the lower halftone side does not exist on the luminance histogram, while in FIG. 4C, the border point b on the higher halftone side does not exist on the luminance histogram. In the following, description will be made on a histogram control method when the brightness of a sample image is biased so that one border point does not appear on the histogram, as described above.

A histogram 402 shown in FIG. 4B illustrates the case where the sample image is short of brightness so that the border point a does not appear on the histogram 402. In this event, a histogram function is calculated, a tangential line 403 is drawn to the curve of the histogram in the lower halftone region, and an intersection a' of the tangential line 403 is located on the halftone level axis. Since the border point a exists within a range from the halftone level a' to halftone level 1, a' is regarded as a virtual border point, and a halftone level at that point is designated a' (<0). The tangential line 403 is connected to the histogram 402 on the lower luminance side to create a virtual histogram. Then, the probe current amount is controlled to a calculated value at which the brightness B (=S/N) is equal to a halftone level X. When the probe currents before and after the control are designated $I_O$, $I_P$, respectively, the aforementioned Equation (2) is satisfied, so that the prove current amount after the control is expressed by the aforementioned Equation (3).

The minimum frame count F is calculated based on the relational expression $I_P \times F = A$ (constant), in a manner similar to FIG. 4A. Then, the dynamic range of the amplifier 118 is adjusted such that a halftone width (b-a') of the histogram is included in 256 levels of halftone to control the contrast. With this control, the histogram 402 is shifted as indicated by a broken-line histogram 404 in FIG. 4B. Since the histogram 404 after the shift includes the two border points, the resulting sample image exhibits a high visibility.

A histogram 405 shown in FIG. 4C illustrates the case where the sample image is so bright that the border point b does not appear on the histogram 405. In this event, a tangential line 406 is drawn to the curve of the histogram 405 in a higher halftone region, and an intersection b' of the tangential line 406 is located on the halftone level axis. Since the border point b exists in a range from halftone level 254 to the halftone level b', b' is assumed to be a virtual border point. Subsequently, a similar method to that used in FIG. 4B is used to calculate the probe current amount at which the brightness B (=S/N) of a virtual histogram, which includes the tangential line 406 connected on the higher luminance side, is equal to a halftone level X by the aforementioned Equation (3) to control the probe current amount. Then, the dynamic range of the amplifier 118 is controlled such that the halftone width (b'-a) of the histogram is included in the 256 levels of halftone to control the contrast. With this control, the histogram 405 is shifted as indicated by a broken-line histogram 407 in FIG. 4C. Since the histogram 407 after the shift includes the two border points, the resulting sample image exhibits a high visibility.

When a resulting histogram is biased to the lower luminance side or higher luminance side as shown in FIG. 4B or 4C, a histogram is created again from a captured image after the probe current amount is controlled and the dynamic range is adjusted, and it is confirmed whether or not the resulting histogram is in a desired shape. The confirmation is made from the presence or absence of the border points on the created histogram, and the brightness. If the histogram is not in the desired shape, another histogram is created again.

Figure 5A:
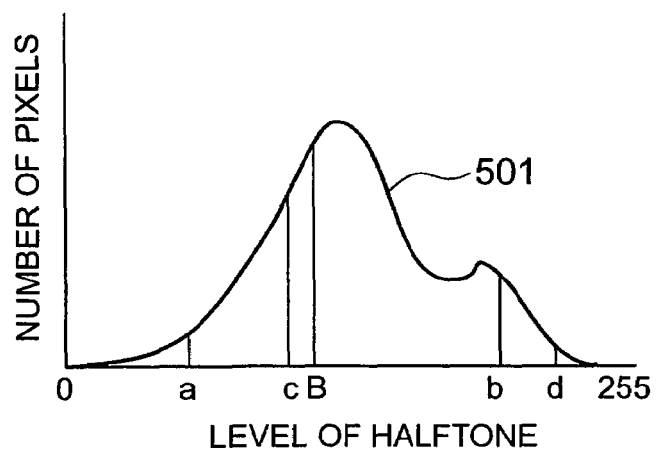
FIGS. 5A-5C are graphs generally showing another exemplary histogram control method.
Figure 5B:
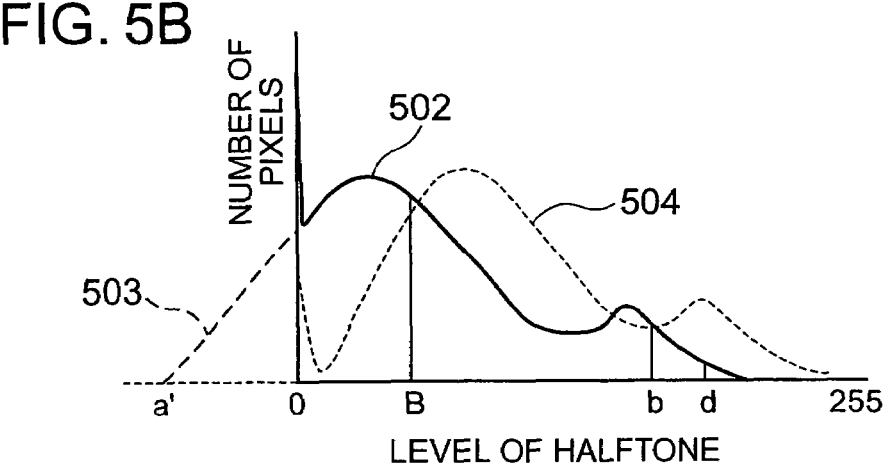
Figure 5C:
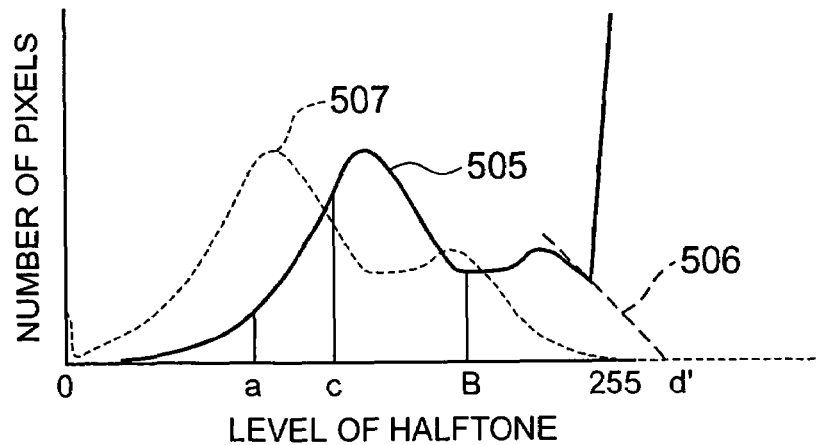

While the foregoing description has been made in connection with a luminance histogram which has one peak, the histogram control can be conducted in a similar manner when a luminance histogram has two or more peaks. Referring now to FIGS. 5A-5C, description will be made on the histogram control for a luminance histogram which has two peaks.

FIG. 5A is a diagram showing an exemplary luminance diagram 501 which has two peaks p1, p2. Such a luminance histogram is created, for example, when a high scaling factor is chosen for a sample image to cause an increase in the number of pixels in a sample region (high luminance region), and is regarded as superimposition of two luminance histograms corresponding to the peaks p1, p2 in the background region and sample region. Then, border points a, b can be assumed for a luminance histogram corresponding to the peak p1, while border points c, d can be assumed for a luminance histogram corresponding to the peak p2. The border points a, b are located at halftone levels at which a second-order differential graph of the luminance histogram corresponding to the peak p1 indicates maxima when the luminance histogram 501 is broken down into two luminance histograms, while the border points c, d are located at halftone levels at which a second-order differential graph of the luminance histogram corresponding to the peak p2 indicates maxima. Since a halftone range between the two border points appearing at both ends of a luminance histogram is important for making an observation, a range of a halftone width ab is important for the background region of the peak p1, and a range of a halftone width cd is important for the sample region of the peak p2. From the foregoing, it can be said that for the luminance histogram having the two peaks p1, p2, a halftone width required for an observation is a range defined by the border points a, d at both ends.

In conclusion, even in a luminance histogram having two peaks, the histogram control only needs to consider the existence of the border points a, d in both end regions of the histogram, so that the histogram 501 is second-order differentiated in both end regions thereof to locate the border points a, d. Then, the histogram control is conducted in the same manner as described with reference to FIGS. 4A-4C, such that the two border points appear on the histogram, and the width of the histogram falls within the 256 levels of halftone.

When border points appear at both ends of a histogram as shown in FIG. 5A, the brightness (average value of the histogram) B of the image is calculated by the aforementioned Equation (1), when S is an area when the histogram is integrated, and N is the total number of pixels. The probe current amount is controlled such that the brightness B is shifted to the position of a halftone level X substantially at the center, for example, halftone level 130. Since the brightness is generally proportional to the probe current, the aforementioned Equation (2) is established, and the probe current amount $I_P$ is found by the aforementioned Equation, where $I_O$ is the probe current before the control is conducted, and $I_P$ is the probe current at which the brightness B reaches a halftone level X. The frame count F is also calculated based on the probe current amount using the relational equation $I_P \times F = A$ (constant) in a manner similar to the foregoing. The constant A differs from one sample to another. The contrast control is conducted by adjusting the dynamic range of the amplifier 118 such that the halftone width (d-a) between the halftone levels a, d at the border points, found by the second-order differential, falls within the 256 levels of halftone.

When the sample image is too dark, the resulting histogram shifts to the left (toward the lower level of halftone) as shown in FIG. 5B, where the number of pixels is increased in a lower halftone end region including halftone level 0, and a peak appears at the lower end of halftone. Conversely, when the sample image is too bright, the histogram shifts to the right (toward the higher level of halftone) as shown in FIG. 5C, where the number of pixels is increased in a higher halftone end region including halftone level 255, and a peak appears at the higher end of halftone. In FIG. 5B, the border point a on the lower halftone side does not exist on the luminance histogram, while in FIG. 5C, the border point d on the higher halftone side does not exist on the luminance histogram. A similar histogram control method to that employed when a luminance histogram has one peak is also employed when the brightness of a sample image is biased so that one border point does not appear on the histogram, as described above.

Specifically, for a histogram 502 shown in FIG. 5B, a histogram function is calculated, a tangential line 503 is drawn to the curve of the histogram in the lower halftone region, and an intersection a' of the tangential line 503 is located on the halftone level axis. The intersection a' is regarded as a virtual border point, and a halftone level at that point is designated a' (<0). The tangential line 503 is connected to the histogram 502 on the lower luminance side to create a virtual histogram. Then, the probe current amount is controlled to a calculated value at which the brightness B (=S/N) is equal to a halftone level X. When the probe currents before and after the control are designated $I_O$, $I_P$, respectively, the aforementioned Equation (2) is satisfied, so that the prove current value after the control is expressed by the aforementioned Equation (3).

The minimum frame count F is calculated based on the relational expression $I_P \times F = A$ (constant). Then, the dynamic range of the amplifier 118 is adjusted such that a halftone width (d-a') of the histogram is included in the 256 levels of halftone to control the contrast. With this control, the histogram 502 is shifted as indicated by a broken-line histogram 504 in FIG. 5B. Since the histogram 504 after the shift includes two border points, the resulting sample image exhibits a high visibility.

A histogram 505 shown in FIG. 5C illustrates the case where the sample image is so bright that the border point d does not appear on the histogram 505. In this event, a tangential line 506 is drawn to the curve of the histogram 505 in a higher halftone region, and an intersection d' of the tangential line 406 is located on the halftone level axis. The intersection b' is assumed to be a virtual border point. Subsequently, a similar method to that used in FIG. 5B is used to calculate the probe current amount at which the brightness B (=S/N) of a virtual histogram, which includes the tangential line 506 connected on the higher luminance side, is equal to a halftone level X by the aforementioned Equation (3) to control the probe current amount. Then, the dynamic range of the amplifier 118 is controlled such that the halftone width (d'-a) of the histogram is included in the 256 levels of halftone to control the contrast. With this control, the histogram 505 is shifted as indicated by a broken-line histogram 507 in FIG. 5C. Since the histogram 507 after the shift includes two border points, the resulting sample image exhibits a high visibility.

When a resulting histogram is biased to the lower luminance side or higher luminance side as shown in FIG. 5B or 5C, a histogram is created again from a captured image after the probe current amount is controlled and the dynamic range is adjusted, and it is confirmed whether or not the resulting histogram is in a desired shape. The confirmation is made from the presence or absence of the border points on the created histogram, and the brightness. If the histogram is not in the desired shape, another histogram is created again.

Figure 6:
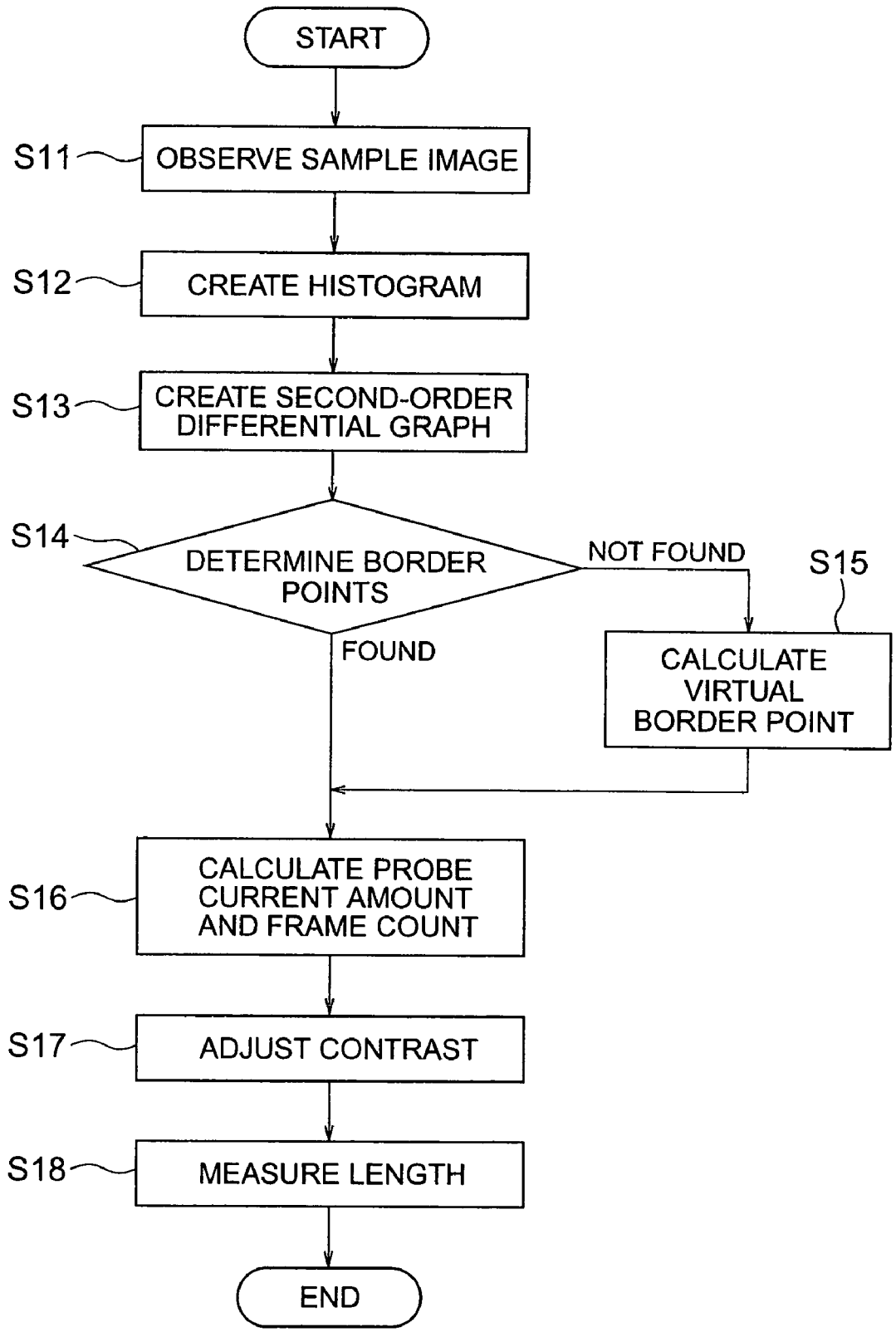
FIG. 6 is a flow chart illustrating a procedure for image acquisition based on the histogram control length measurement using the image.

FIG. 6 is a flow chart illustrating a procedure of image acquisition based on the histogram control described above, and a measurement (length measurement) using this image. First, a sample image is observed (S11). Next, a luminance histogram is created from the sample image (S12). A second-order differential graph is created from the luminance histogram (S13), and it is determined whether or not border points of the background and sample appear on the lower luminance side and higher luminance side, respectively (S14). If any of the border points does not appear, a virtual border point is calculated as described in connection with FIGS. 4B, 4C or FIGS. 5B, 5C (S15). Subsequently, the probe current amount is calculated such that the brightness of the image is substantially equal to a median value of the halftone range, and the frame count is calculated corresponding to the probe current amount (S16). The calculated probe current amount and frame count may be displayed on a monitor screen. Next, the dynamic range of the amplifier 118 is adjusted to achieve an appropriate contrast (S17). Finally, a sample image is formed using the probe current amount and the frame count calculated at step 16 to make a length measurement (S18).

Figure 7:
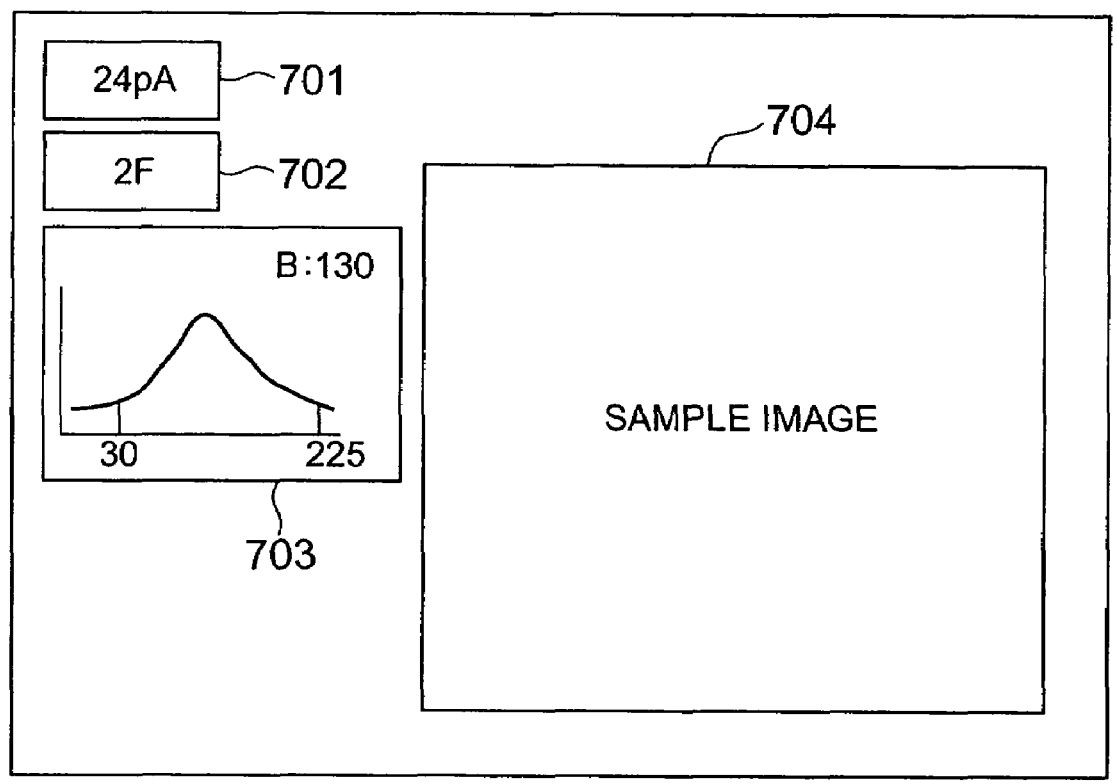
FIG. 7 is a diagram illustrating an example of display screen of sample image unit.

FIG. 7 is a diagram illustrating an exemplary display screen of the sample image display unit 121. In this example, the user can confirm the probe current amount 701, the frame count 702, and a re-created histogram 703 on the display screen. Border points and brightness are associated with the displayed histogram 703, allowing the user to confirm the histogram. A sample image for length measurement is displayed in a window 704.

The histogram adjusting method described above can provide a histogram in which border points of a background and a sample appear within a halftone range of levels 0-255. Then, the prove current amount which provides an appropriate brightness for the sample image can be calculated based on the border points, and a minimum frame count can be calculated in accordance with the probe current amount, thus controlling a highly visible sample image.

When length measurements were made ten times in accordance with the low frame scanning scheme of the present invention with the number of frames reduced from conventional 16 to four and the probe current amount increased from 8 pA to 25 pA, the amount of slimming could be reduced from 6.7 nm to 3.0 nm. When the second length measurement was made, the slimming could be reduced from 1.3 nm to 0.3 nm. The length measurement repeatable accuracy (3σ) is 0.7 nm which satisfies an allowable range.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A method of adjusting a condition of an electron beam when an image is formed by scanning said electron beam on a sample, and detecting secondary electrons emitted by the sample, and accumulating a plurality of frames obtained by said scanning, comprising the steps of:

forming a luminance histogram of the image obtained by scanning said electron beam; and adjusting a current of said electron beam so that a brightness of said image obtained by the formed luminance histogram corresponds to a predetermined gray-scale.

2. A method of adjusting condition of the electron beam according to claim 1, wherein said number of frames to be accumulated is determined so that a result of multiplication of said number of frames to be accumulated and a current of said adjusted electron beam equals to a predetermined constant number.

3. A method of adjusting condition of the electron beam according to claim 2, wherein said constant number is different according to a kind of a sample.

4. A scanning electron microscope comprising:
an electron beam source;
a lens for converging an electron beam emitted from said electron beam source onto a sample;
a scanning deflector for scanning an electron beam converged on said sample on the basis of a number of accumulation frames set;
a detector for detecting electrons emitted from said sample; and
a controller for forming a luminance histogram of an image obtained by scanning said electron beam, and adjusting a current of said electron beam so tat a brightness of said image obtained by the formed luminance histogram corresponds to a predetermined gray-scale.

5. A scanning electron microscope according to claim 4, wherein said controller has a function for determining said number of accumulation frames so that a result of multiplication of a number of accumulation frames and said current of said electron beam equals to a predetermined constant number.

6. A scanning electron microscope according to claim 5, wherein said controller comprises different constant numbers for each kind of said sample.

7. A scanning electron microscope comprising:
an electron beam source;
a lens for converging an electron beam emitted from said electron beam source onto a sample;
a scanning deflector for scanning an electron beam converged on said sample on the basis of a number of accumulation frames set;
a detector for detecting electrons emitted from said sample; and
a controller for forming an image on the basis of said electrons detected by said detector, said controller having functions for determining said number of said accumulation frames on the basis of a current of said electron beam and a constant number representing a relation between said current of said electron beam and a number of accumulation frames, said constant number being different according for each kind of said sample.

8. A scanning electron microscope according to claim 7, said constant number is a product of multiplication of said current of said electron beam and said number of accumulation frames.

9. A method of adjusting condition of the electron beam according to claim 1, wherein a number of the frames is determined based on a relational expression between the adjusted electron beam current and the number of frames.

10. A scanning electron microscope according to claim 4, wherein a number of the frames is determined based on a relational expression between the adjusted electron beam current and the number of frames.

* * * * *